United States Patent [19]

Burch et al.

[11] Patent Number: 5,023,272
[45] Date of Patent: Jun. 11, 1991

[54] USE OF 5-PHENYL-2-FURAN ESTERS AND AMIDES AS ANTIEPILEPTIC AGENTS

[75] Inventors: Homer A. Burch, Norwich; Alan W. Castellion, Oxford; Stanford S. Pelosi, Jr., Norwich, all of N.Y.

[73] Assignee: Norwich Eaton Pharmaceuticals, Inc., Norwich, N.Y.

[21] Appl. No.: 371,355

[22] Filed: Jun. 23, 1989

[51] Int. Cl.$^5$ .................. C07D 307/52; C07D 307/54; A61K 31/34
[52] U.S. Cl. .................................... 514/471; 549/484; 549/487; 544/152; 544/379; 546/214
[58] Field of Search ................. 549/484, 487; 514/471

[56] References Cited

U.S. PATENT DOCUMENTS

| | | | |
|---|---|---|---|
| 3,856,825 | 12/1974 | Wright et al. | 549/484 |
| 4,035,394 | 7/1977 | Pelosi, Jr. et al. | 549/488 |
| 4,128,550 | 12/1978 | Pelosi, Jr. et al. | 546/214 |
| 4,162,257 | 7/1979 | Pelosi, Jr. et al. | 549/487 |
| 4,403,097 | 9/1983 | Pelosi, Jr. et al. | 549/487 |
| 4,643,996 | 2/1987 | Pelosi, Jr. et al. | 514/471 |

OTHER PUBLICATIONS

Oleinik, A. E. et al., "Synthesis and Tuberculostatic Activity of 5-Arylpyromucic Acid Derivatives", *Pharmaceutical Chemical Journal*, vol. 10, No. 4, (Apr. 1976), pp. 463–465.
Burch, H., R. White, G. Wright & M. Goldenberg, "Phenyl Furans IV: Spasmolytic 3-Diethylamino-2,-2-(Dimethyl)Propyl Esters of 5-Substituted Phenyl-2-Furancarboxylic Acids", *Journal of Pharmaceutical Sciences*, vol. 69, No. 1, (Jan. 1980), pp. 107–110.
Goldenberg, M., "F-461, 3-Diethylamino-2,2-Dimethylpropyl 5-(P-Nitrophenyl)-2-Furoate Hydrochloride, a New Non-Anticholinergic Spasmolytic and a Gastric Acid Inhibitor", *Arch. Int. Pharmacodyn*, vol. 222, pp. 27–39 (1976).

Primary Examiner—Mukund J. Shah
Assistant Examiner—Philip I. Datlow
Attorney, Agent, or Firm—David L. Suter; Karen F. Clark; Jack D. Schaeffer

[57] ABSTRACT

A method of preventing epileptic seizures in a human or mammal subject susceptible to said seizures, comprising systemically administering to said subject a safe and effective amount of a compound of the formula:

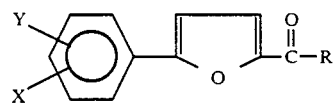

wherein
(a) X is halo or hydrogen, and Y is a substituent selected from the group consisting of unsubstituted or halogen-substituted methyl, halo, nitro, amino, and methoxy; and
(b) R is $N(R^3)_2$, $OR^1N(R^3)_2$, $N(R^2)R^1N(R^3)_2$, or $N(R^2)N(R^3)_2$; where
$R^1$ is $C_1$-$C_3$ alkylene which is unsubstituted or substituted with $C_1$-$C_2$ alkyl;
$R^2$ is hydrogen or lower alkyl; and
each $R^3$ is, independently, hydrogen or lower alkyl; or both $R^3$ groups are connected to form a saturated 5- or 6-membered heterocycle containing 1 or 2 heteroatoms selected from oxygen and nitrogen and said heterocycle is unsubstituted or substituted with lower alkyl or hydroxy-substituted lower alkyl;
or a pharmaceutically-acceptable salt thereof.

Preferably X is halo, preferably Y is trifluoromethyl, and R is preferably 3-diethylamino-2,2-dimethylpropoxy.

11 Claims, No Drawings

USE OF 5-PHENYL-2-FURAN ESTERS AND AMIDES AS ANTIEPILEPTIC AGENTS

BACKGROUND OF THE INVENTION

This invention relates to certain novel 5-phenyl-2-furan esters and amides and the novel use of these and related compounds as antiepileptic agents.

Antiepileptic agents are used to treat seizure disorders. Approximately 2.5 million of all Americans have epilepsy. Epilepsy often begins in childhood, with three quarters of the patients having their first seizure before the age of 18. Two hundred thousand Americans have epileptic seizures more than once a month. Most epileptic patients are dependent on drugs to control seizures, but therapy is often inadequate. For certain types of seizures there are no specific drugs available.

The modern history of antiepileptic drugs marketed in the United States began in 1912 with the introduction of phenobarbital, a synthetic sedative-hypnotic drug which was shown to reduce seizure frequency. Since the barbituric acid molecule is easily modified, many analogs of phenobarbital were synthesized and marketed for antiepileptic activity. Antiepileptic drug development then entered a dormant period lasting for twelve years, from 1961 to 1973, during which the only new drug of interest was diazepam, an adjunctive drug used mostly in status epilepticus.

In 1968, the Epilepsy Branch of the National Institute of Neurological and Communicative Disorders attempted to reverse the decline in antiepileptic drug development by conducting controlled clinical trials of several drugs that needed proof of efficacy. The resulting data eventually supported new drug applications for carbamazepine in 1974, clonazepam in 1975 and valproic acid in 1978.

Many patients with common types of seizures and most of those with rare types fail to respond to available drugs and/or suffer adverse side effects. The currently available antiepileptic drugs have many adverse side effects. They include cardiovascular collapse, central nervous system depression, aplastic anemia, congestive heart failure, visual hallucinations, liver damage, impaired cognition, ataxia, personality changes, psychosis, aggressive behavior, nausea, dizziness and sedative effects. For those patients whose seizures are controlled with currently available therapy, a new drug may allow a reduction in the adverse side effects. It has been discovered that certain 5-phenyl-2-furan esters and amides have antiepileptic activity. These compounds are potentially less toxic and/or have greater efficacy than current agents used clinically as antiepileptic agents.

A number of phenyl furans are described in the literature. However, these compounds have never been suggested to have antiepileptic activity. For example, U.S. Pat. No. 3,856,825 issued to Wright et al. on Dec. 24, 1974, discloses a series of 3-diethylamino-2,2-dimethylpropyl 5-(substituted phenyl)-2-furoates that possess pharmacological properties, particularly being useful as antispasmodics. U.S. Pat. No. 4,162,257 issued to Pelosi and Yu on July 24, 1979, discloses N,N-dimethyl-5-phenyl-2-furamides said to be useful as anti-inflammatory agents. Oleinik, A. F. et al., "Synthesis and Tuberculostatic Activity of 5-Arylpyromucic Acid Derivatives", *Pharmaceutic Chemical Journal*, Vol. 10, No. 4 (April, 1976), pages 463–465, discloses certain 5-phenyl-2-furans said to have bacteriostatic activity.

SUMMARY OF THE INVENTION

The present invention encompasses certain novel 5-phenyl-2-furan esters and amides and compositions thereof. It also encompasses methods for preventing epileptic seizures in a human or other mammal susceptible to such seizures, using these compounds and related compounds. These methods comprise systemically administering to such human or mammal subject a safe and effective amount of a compound of the formula:

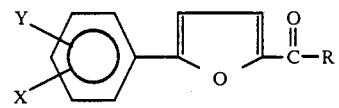

wherein (1) X is halo or hydrogen; and Y is a substituent selected from the group consisting of unsubstituted or halogen-substituted methyl, halo, nitro, amino, and methoxy; and (2) R is $N(R^3)_2$, $OR^1N(R^3)_2$, $N(R^2)R^1N(R^3)_2$, or $N(R^2)N(R^3)_2$; where $R^1$ is $C_1$–$C_3$ alkylene which is unsubstituted or substituted with $C_1$–$C_2$ alkyl;

$R^2$ is hydrogen or lower alkyl; and each $R^3$ is, independently, hydrogen or lower alkyl; or both $R^3$ groups are connected to form a saturated 5- or 6-membered heterocycle containing 1 or 2 heteroatoms selected from oxygen and nitrogen, and said heterocycle is unsubstituted or substituted with lower alkyl or hydroxy-substituted lower alkyl;

or a pharmaceutically-acceptable salt thereof.

DESCRIPTION OF THE INVENTION

The present invention encompasses certain novel 5-phenyl-2-furan esters and amides and compositions using these and related compounds. It also encompasses methods for preventing epileptic seizures in a human or mammal subject susceptible to such seizures, using these compounds and related compounds. Specific compounds and compositions to be used in the invention must, accordingly, be pharmaceutically acceptable. As used herein, such a "pharmaceutically-acceptable" component is one that is suitable for use with humans and/or animals without undue adverse side effects (such as toxicity, irritation, and allergic response) commensurate with a reasonable benefit/risk ratio.

METHODS OF TREATMENT

The present invention encompasses a method of preventing epileptic seizures in a human or mammal subject susceptible to said seizures which comprises systemically administering to said subject a safe and effective amount of a compound (hereinafter referred to as a "5-phenyl furan") of the chemical structure:

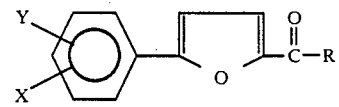

wherein (1) X is halo or hydrogen; and Y is a substituent selected from the group consisting of unsubstituted or halogen-substituted methyl, halo, nitro, amino, and methoxy; and (2) R is $N(R^3)_2$, $OR^1N(R^3)_2$, $N(R^2)R^1N(R^3)_2$, or $N(R^2)N(R^3)_2$; where $R^1$ is $C_1$–$C_3$ alkylene which is unsubstituted or substituted with $C_1$–$C_2$ alkyl;

$R^2$ is hydrogen or lower alkyl; and each $R^3$ is, independently, hydrogen or lower alkyl; or both $R^3$ groups are connected to form a saturated 5- or 6-membered heterocycle containing 1 or 2 heteroatoms selected from oxygen and nitrogen, and said heterocycle is unsubstituted or substituted with lower alkyl or hydroxy-substituted lower alkyl;

or a pharmaceutically-acceptable salt thereof. "Lower alkyl" is a 1 to 6 carbon chain; preferably a 1 to 3 carbon chain.

Typically, the dosage regimen consists of administration of a 5-phenyl furan one to four times per day. Preferably, the 5-phenyl furan will be administered two to four times per day. More preferably, the 5-phenyl furan will be administered once daily. Treatment regimens can extend for the life of the subject depending upon the type of epileptic seizure to which the subject is susceptible.

The 5-phenyl-furans and compositions of the instant invention are preferably administered systemically, i.e., through any method of introducing the 5-phenyl-furan into the tissues of the body, e.g., intrathecal, epidural, intramuscular, transdermal, intravenous, intraperitoneal, subcutaneous, sublingual, and oral administration. Preferred methods of parenteral administration are through intravenous or intramuscular injections. As is known and practiced in the art, all formulations for parenteral administration must be sterile. For mammals, especially humans, (assuming an approximate body weight of 70 kg) individual doses of from about 0.1 mg to about 2 g of 5-phenyl-furan are acceptable. Individual doses of from about 0.1 mg to about 1 g are preferred.

A preferred method of systemic application of the 5-phenyl-furan is through oral administration. For mammals, especially humans, (assuming an approximate body weight of 70 kg) individual doses of from about 0.1 mg to about 2 g of 5-phenyl furan are acceptable. Individual doses of from about 0.1 mg to about 1 g are preferred. The most preferred dosing regimen is once or twice per day and the most preferred unit dosage form is 0.1 mg to 500 mg.

A "safe and effective amount" of a 5-phenyl furan is an amount that is effective to inhibit epileptic seizures in a human or mammal subject susceptible to said epileptic seizures, without undue adverse side effects (such as toxicity, irritation, or allergic response), commensurate with a reasonable benefit/risk ratio when used in the manner of this invention. This specific "safe and effective amount" will, obviously, vary with such factors as the particular type of epilepsy being treated, the physical condition of the patient, the duration of treatment, the nature of concurrent therapy (if any), the specific dosage form to be used, the carrier employed, and the dosage regimen desired for the composition.

As used herein, "epileptic seizures" refer to changes in behavior or activity caused by an excessive electrical discharge in the brain cells. A susceptibility to excessive electrical discharge in the brain cells can be due to genetic inheritance, exposure to chemical toxins, disease or accident. The varieties of seizures are almost infinite because any area of the brain can be affected by the abnormal electrical discharge.

Epilepsy is not a disease in and of itself, but rather it is a collective designation for a group of chronic central nervous system disorders that are characterized by the occurrence of sudden and transitory episodes, called seizures. A person with epilepsy has recurrent seizures. Any disease, toxin or accident that affects the central nervous system can cause a seizure. Information on epilepsy can be found in *Epilepsy*, by Allen H. Middleton et al. (1981) incorporated herein by reference.

The International Classification of Epileptic Seizures classifies seizures into those that have a partial or focal onset in one area of the brain and those that have a generalized onset. There are two primary types of partial seizures: those with elementary symptomatology and those with complex symptomatology. Partial seizures with elementary symptomatology are caused by an abnormal electrical discharge that starts in one certain area of the brain; the clinical manifestations brought about by this discharge depend upon the specific area of the brain involved. For example, if the seizure involves the motor cortex, the clinical change may be a single jerk or multiple jerks of the arm or leg. Partial seizures with elementary symptomatology generally do not spread to areas of the brain involved with consciousness.

Another subcategory of focal-onset seizures is partial seizures with complex symptomatology (often called "partial complex"). A partial complex seizure is one in which abnormal discharges usually occur in both temporal lobes. Since the temporal lobes govern memory and alertness, the person experiences an impairment of consciousness.

A further subcategory is "partial seizures secondarily generalized." A seizure discharge can start in one focal area of the brain and if it spreads out to the rest of the brain the person can have a secondarily generalized tonic-clonic (grand mal) seizure. This is akin to a chain reaction wherein the abnormal discharge that begins in a few brain cells causes more and more brain cells to have abnormal discharges until the whole brain is involved.

The second major class of seizures is "generalized onset seizures." These begin without a focal onset and affect both sides of the body. In this category are found the two classic types of epilepsy: absence seizures (also referred to as petit mal seizures), and generalized tonic-clonic seizures (also referred to as grand mal seizures). In the absence seizure, the patient stares ahead for a brief period (5 to 15 seconds). After the episode, the person will probably resume what he was doing and may not be aware of the brief interruption. The patient undergoing a generalized tonic-clonic seizure usually stiffens for 30 to 60 seconds and then jerks for a similar period; or the stiffening and jerking may alternate irregularly. Tonic refers to a stiffening of the body and clonic refers to a jerking of the body. The name "generalized tonic-clonic" is derived from the lack of focal onset of the seizure and the stiffening and jerking motions during the seizure. The patient undergoing this type of seizure will also lose consciousness and fall.

Some 5-phenyl furans useful in these methods are described in issued U.S. Patents and scientific literature. For example, U.S. Pat. No. 4,162,257 by Pelosi and Yu issued on July 24, 1979, discloses N,N-dimethyl-5-phenyl-2-furamides that conform to the formula of the compound of this invention wherein X is nil and Y is either amino or chloro and R is $N(R^3)_2$, and wherein $R^3$ is methyl. The compounds of the '257 patent are said to act as anti-inflammatory agents. U.S. Pat. No. 3,856,825 by Wright et al. issued on Dec. 24, 1974, discloses a series of 3-diethyl amino-2,2-dimethylpropyl 5-(substituted phenyl)-2-furoates that conform to the formula of the compound of the present invention wherein X is nil, Y is a member of the group consisting of 4-nitro, 4-trifluoromethyl, 3,4-difluoro, 3-methoxy, 4-methyl, 4-methoxy, 4-bromo, 2,3-dichloro, 2-nitro-4-methyl, and 4-chloro; R is $OR^1N(R^3)_2$, and $R^1$ is propyl disubstituted with methyl and $R^3$ is ethyl. The compounds of the '825 patent are said to possess antispasmodic activity. "Synthesis and Tuberculostatic Activity of 5-Arylpyromucic Acid Derivatives", *Pharmaceutical Chemical Journal* Vol 10, No. 4 (April, 1976), by Oleinik et al. discloses 5-arylfuran-2-carboxylic acids and their derivatives. The 5-arylfuran-2-carboxylic acid hydrazides and esters are said to possess bacteriostatic activity against the tuberculosis bacillus. U.S. Pat. No. 4,162,257 and U.S. Pat. No. 3,856,825 and "Synthesis and Tuberculostatic Activity of 5-Arylpyromucic Acid Derivatives" by Oleinik et al. are incorporated by reference herein.

Preferred 5-phenyl furans useful in this method include those compounds wherein X is a meta or para substituent and is selected from the group consisting of fluoro, chloro, and bromo. Preferred 5-phenyl-furans also include those compounds wherein Y is selected from the group consisting of fluoro, chloro, halogen substituted methyl and methoxy. A particularly preferred 5-phenyl furan is one wherein Y is trifluoromethyl. Further preferred 5-phenyl-furans include those compounds wherein $R^3$ is selected from the group consisting of hydrogen, methyl and ethyl and $R^1$ is 2,2-dimethylpropyl. Preferred compounds useful in the methods of this invention include:

3-diethylamino-2,2-dimethylpropyl 5-(p-nitrophenyl)-2-furoate hydrochloride; 3-diethylamino-2,2-dimethylpropyl 5-(p-aminophenyl)-2-furoate dihydrochloride; 3-diethylamino-2,2-dimethylpropyl 5-(o-chlorophenyl)-2-furoate hydrochloride; 3-diethylamino-2,2-dimethylpropyl 5-(p-fluorophenyl)-2-furoate hydrochloride; 3-(diethylamino)-2,2-dimethylpropyl 5-(4-chlorophenyl)-2-furancarboxylate hydrochloride; 3-diethylamino-2,2-dimethylpropyl 5-(2,3-dichlorophenyl)-2-furoate hydrochloride; 3-diethylamino-2,2-dimethylpropyl 5-(3,4-dichlorophenyl)-2-furoate hydrochloride; 3-diethylamino-2,2-dimethylpropyl 5-(4-chloro-2-nitrophenyl)-2-furoate hydrochloride; 3-diethylamino-2,2-dimethylpropyl 5-(m-trifluoromethylphenyl)-2-furoate hydrochloride; 3-diethylamino-2,2-dimethylpropyl 5-(m-nitrophenyl)-2-furoate hydrochloride; 3-diethylamino-2,2-dimethylpropyl 5-(p-bromophenyl)-2-furoate hydrochloride; 3-diethylamino-2,2-dimethylpropyl 5-(p-methoxyphenyl)-2-furoate hydrochloride; 3-diethylamino-2,2-dimethylpropyl 5-(m-methoxyphenyl)-2-furoate fumarate; 3-diethylamino-2,2-dimethylpropyl 5-(p-trifluoromethylphenyl)-2-furoate hydrochloride; 3-diethylamino-2,2-dimethylpropyl 5-(p-methylphenyl)-2-furoate fumarate; 3-diethylamino-2,2-dimethylpropyl 5-(3,4-difluorophenyl)-2-furancarboxylate hydrochloride hemihydrate; 3-diethylamino-2,2-diethylpropyl 5-(p-nitrophenyl)-2-furoate hydrochloride; 1-methyl-4-piperidyl 5-(p-chlorophenyl)-2-furoate hydrochloride; 5-(p-chlorophenyl)-2-furamide; 5-(p-chlorophenyl)-N,N-dimethyl-2-furamide; 5-(p-chlorophenyl)-2-furoic acid 1-isopropylhydrazide; 5-(4-aminophenyl)-N-[2-(diethylamino)ethyl]-2-furancarboxamide hydrochloride; N-[3-(diethylamino)-2,2-dimethylpropyl]-5-(4-trifluoromethylphenyl)-2-furancarboxamide (Z)-2-butenedioic acid salt; 5-(4-bromophenyl)-N-[3-(4-morpholinyl)propyl]-2-furancarboxamide hydrate; 5-(2,4-dichlorophenyl)-N-[3-(4-morpholinyl)propyl]-2-furancarboxamide hydrochloride hydrate; 1-[5-(4-nitrophenyl)-2-furanylcarbonyl]piperazine hydrobromide; N-(3-diethylamino-2,2-dimethylpropyl)-5-(p-chlorophenyl)-2-furamide hydrochloride; 5-(m-trifluoromethylphenyl)-2-furoic acid hydrazide.

More preferred 5-phenyl furans useful in this method include:

3-diethylamino-2,2-dimethylpropyl 5-(p-nitrophenyl)-2-furoate hydrochloride; 3-diethylamino-2,2-dimethylpropyl 5-(p-fluorophenyl)-2-furoate hydrochloride; 3-(diethylamino)-2,2-dimethylpropyl 5-(4-chlorophenyl)-2-furancarboxylate hydrochloride; 3-diethylamino-2,2-dimethylpropyl 5-(3,4-dichlorophenyl)-2-furoate hydrochloride; 3-diethylamino-2,2-dimethylpropyl 5-(4-chloro-2-nitrophenyl)-2-furoate hydrochloride; 3-diethylamino-2,2-dimethylpropyl 5-(m-trifluoromethylphenyl)-2-furoate hydrochloride; 3-diethylamino-2,2-dimethylpropyl 5-(m-nitrophenyl)-2-furoate hydrochloride; 3-diethylamino-2,2-dimethylpropyl 5-(p-bromophenyl)-2-furoate hydrochloride; 3-diethylamino-2,2-dimethylpropyl 5-(p-methoxyphenyl)-2-furoate hydrochloride; 3-diethylamino-2,2-dimethylpropyl 5-(m-methoxyphenyl)-2-furoate fumarate; 3-diethylamino-2,2-dimethylpropyl 5-(p-trifluoromethylphenyl)-2-furoate hydrochloride; 3-diethylamino-2,2-dimethylpropyl 5-(p-methylphenyl)-2-furoate fumarate; 3-diethylamino-2,2-dimethylpropyl 5-(3,4-difluorophenyl)-2-furancarboxylate hydrochloride hemihydrate; 1-methyl-4-piperidyl 5-(p-chlorophenyl)-2-furoate hydrochloride; 5-(p-chlorophenyl)-2-furamide; 5-(p-chlorophenyl)-N,N-dimethyl-2-furamide; 5-(p-chlorophenyl)-2-furoic acid 1-isopropylhydrazide; 5-(4-aminophenyl)-N-[2-(diethylamino)ethyl]-2-furancarboxamide hydrochloride; N-[3-(diethylamino)-2,2-dimethylpropyl]-5-(4-trifluoromethylphenyl)-2-furancarboxamide (Z)-2-butenedioic acid salt; 5-(4-bromophenyl)-N-[3-(4-morpholinyl)propyl]-2-furancarboxamide hydrate; 5-(2,4-dichlorophenyl)-N-[3-(4-morpholinyl)propyl]-2-furancarboxamide hydrochloride hydrate; 1-[5-(4-nitrophenyl)-2-furanylcarbonyl]piperazine hydrobromide; N-(3-diethylamino-2,2-dimethylpropyl)-5-(p-chlorophenyl)-2-furamide hydrochloride; 5-(m-trifluoromethylphenyl)-2-furoic acid hydrazide.

Particularly preferred is 3-diethylamino-2,2-dimethylpropyl 5-(p-trifluoromethylphenyl)-2-furoate hydrochloride.

As used herein, the number 2 and number 6 labeled position on the phenyl group are collectively referred to as the "ortho" or "o" position; the number 5 and number 3 labeled position are collectively referred to as the "meta" or "m" position; and the number 4 labeled position is referred to as the "para" or "p" position.

COMPOUNDS

The present invention also provides "novel 5-phenyl furans" of the formula:

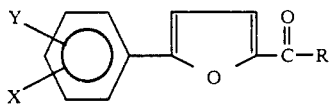

wherein (1) X is halogen or nil; and Y is a substituent selected from the group consisting of unsubstituted or halogen-substituted methyl, halogen, nitro, amino, and methoxy; and (2) R is $N(R^3)_2$, $OR^1N(R^3)_2$, $N(R^2)R^1N(R^3)_2$, or $N(R^2)N(R^3)_2$; where $R^1$ is $C_1$-$C_3$ alkyl which is unsubstituted or substituted with $C_1$-$C_2$ alkyl;

$R^2$ is hydrogen or lower alkyl; and both $R^3$ groups are connected to form a saturated 5- or 6-membered heterocycle containing 1 or 2 heteroatoms selected from oxygen and nitrogen, and said heterocycle is unsubstituted or substituted with lower alkyl or hydroxy-substituted lower alkyl; or a pharmaceutically-acceptable salt thereof. "Lower alkyl" is a 1 to 6 carbon chain; preferably a 1 to 3 carbon chain.

Preferred heterocycles are piperidine, pyridine, and pyrollidine. Some preferred novel 5-phenyl furans useful include those compounds wherein X is selected from the group consisting of fluoro, chloro, and bromo. Other preferred novel 5-phenyl furans include those wherein Y is chloro. Preferred novel 5-phenyl furans useful also include:

5-(4-bromophenyl)-N-[3-(4-morpholinyl)propyl]-2-furancarboxamine hydrate; 5-(2,4-dichlorophenyl)-N-[3-(4-morpholinyl)propyl]-2-furancarboxamide hydrochloride hydrate; 1-[5-(4-nitrophenyl)-2-furanylcarbonyl]piperazine hydrobromide; N-(1-piperidinyl)-5-(4-trifluoromethylphenyl)-2-furancarboxamide; 1-methyl-4-piperidyl 5-(4-methoxyphenyl)-2-furoate; 2-(1-pyrrolidinyl)ethyl 5-(3,4-difluoro-phenyl)-2-furoate.

More preferred novel 5-phenyl furan compounds include: 5-(4-bromophenyl)-N-[3-(4-morpholinyl)propyl]-2-furancarboxamine hydrate; 5-(2,4-dichlorophenyl)-N-[3-(4-morpholinyl)propyl]-2-furancarboxamide hydrochloride hydrate; 1-[5-(4-nitrophenyl)-2-furanylcarbonyl]piperazine hydrobromide.

The compounds of this invention are readily prepared by methods well-known in the chemical literature. Preferably a substituted 5-phenyl-2-furoyl chloride is reacted with an appropriately substituted alcohol or amine in the presence of a solvent such as toluene to prepare the 5-phenyl-2-furyl-esters and 5-phenyl-2-furyl amides, respectively. Amino substituted compounds are prepared by reduction of the nitro to the amino groups in the presence of palladium-on-charcoal and a solvent such as alcohol.

COMPOSITIONS

The present invention also provides compositions for lessening the severity or frequency of epileptic seizures, comprising:

(a) a safe and effective amount of a novel 5-phenyl furan ester or amide; and (b) a pharmaceutically-acceptable carrier.

The compositions of this invention are preferably provided in unit dosage form. As used herein, a "unit dosage form" is a composition of this invention containing an amount of a novel 5-phenyl furan or its pharmaceutically-acceptable salts or hydrates that is suitable for administration to a human or lower animal, in a single dose, according to good medical practice.

The unit dosage form will typically contain from 0.1 mg to 2 g of a novel 5-phenyl furan. Preferably, the unit dosage form will be from 0.1 mg to 1000 mg of a novel 5-phenyl furan. More preferably, the unit dosage form will be from 0.1 mg to 500 mg of a novel 5-phenyl furan.

The compositions of this invention may be in any of a variety of forms. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the anticonvulsant activity of the 5-phenyl furan. The amount of carrier employed in conjunction with the 5-phenyl furan is sufficient to provide a practical quantity of material for administration per unit dose of the 5-phenyl furan. Techniques and compositions for making dosage forms useful in the methods of this invention are described in the following references, all incorporated by reference herein: 7 *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2nd Edition (1976).

In particular, pharmaceutically-acceptable carriers for systemic administration include water, sugars, starches, cellulose and its derivatives, malt, gelatin, talc, calcium sulfate, vegetable oils, synthetic oils, polyols, alginic acid, phosphate buffer solutions, emulsifiers, isotonic saline, pyrogen-free water, fixed oils, isopropyl myristate, benzyl benzoate, dioxolones, glycofurol, dimethylacetamide, N-(β-hydroxyethyl)-lactamide, ethyl lactate, polyethylene glycols, glycerin, 1,3 butylene glycol or a mixture of two or more of the above carriers. Preferred carriers for parenteral administration include aqueous and non-aqueous vehicles containing water, propylene glycol, ethyl oleate, pyrrolidone, ethanol, and sesame oil and mixtures thereof. Preferably, the pharmaceutically-acceptable carrier, in compositions for parenteral administration, comprises at least about 90% by weight of the total composition. Pharmaceutically-acceptable carriers useful in the methods of this invention are described in *Journal of Pharmaceutical Sciences*, p. 917 (October, 1963), which is incorporated by reference herein.

The following non-limiting examples illustrate the compounds, compositions and uses of the present invention.

EXAMPLE I

3-Diethylamino-2,2-dimethylpropyl 5-(p-Fluorophenyl)-2-furoate Hydrochloride

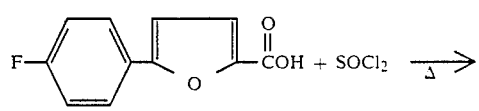

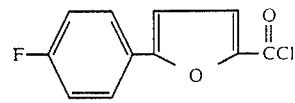

-continued

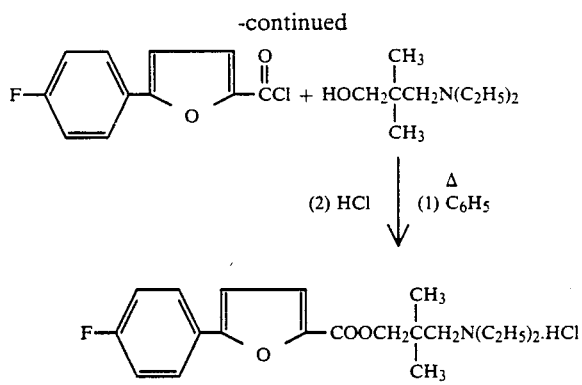

(2) HCl  (1) C₆H₅  Δ

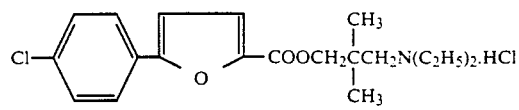

5-(p-Fluorophenyl)-2-furoic acid (18.6 g., 0.09 mole) is added with rapid stirring to thionyl chloride (31.5 ml.) at room temperature, heated until solution occurs (about ¼ hr.) and then is refluxed for 2 hr. The mixture is stripped of excess thionyl chloride in vacuo, benzene (100 ml.) is added, and again stripped of solvent. The residue is treated with a solution of 3-diethylamino-2,2-dimethylpropanol (14.5 g. 0.09 mole) in benzene (490 ml.), is refluxed for 3 hr., cooled, is diluted with petroleum ether (300 ml.), and is stored for 2 days at room temperature. The benzene- petroleum ether solution is decanted, the residue dissolved in H₂O (750 ml.) and the solution adjusted to pH 8 with saturated aqueous Na₂CO₃ (75 ml.). The product is extracted from the aqueous phase with benzene (860 ml.) in portions and the extract dried for 18 hours over MgSO₄ and activated charcoal. The solution is filtered and the filtrate adjusted to pH 3 with ether-HCl (cooled in ice bath). Petroleum ether (400 ml.) is added and the product oiled out of solution. The benzene-petroleum ether solution is decanted and the product washed twice with anhydrous ether (scratching induced crystallization). The solid is recrystallized from isopropanol (200 ml.) to yield 16.9 g. (49%). A sample is recrystallized from isopropanol, m.p. 134°-138°.

One hundred milligrams of the above compound is administered to a human susceptible to generalized tonic-clonic seizures to decrease the frequency and severity of these seizures.

EXAMPLE II

3-Diethylamino-2,2-dimethylpropyl 5-(p-Chlorophenyl)-2-furoate Hydrochloride

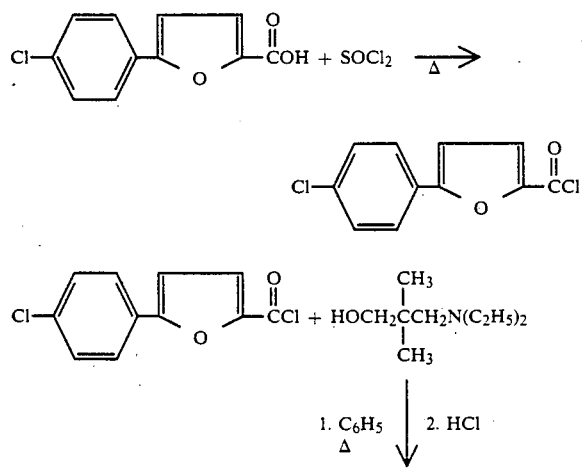

1. C₆H₅  Δ  2. HCl 5-(p-Chlorophenyl)-2-furoic acid (33.5 g., 0.15 mole) is added with rapid stirring to thionyl chloride (58 ml.) at room temperature, heated until solution occurs (about 20 min.) and then refluxed for 2 hr. The mixture is stripped of excess thionyl chloride in vacuo, benzene (100 ml.) is added, and again stripped of solvent. The residue is treated with a solution of 3-diethylamino-2,2-dimethylpropanol (24.1 g., 0.15 mole) in benzene (700 ml.), refluxed for 4 hr., cooled, diluted with petroleum ether (450 ml.) and stored for 18 hours at room temperature. The benzene-petroleum ether solution is decanted, the residue is dissolved in H₂O (1000 ml.), and the solution is adjusted to pH 8 with saturated aqueous Na₂CO₃(70 ml.). The product is extracted from the aqueous phase with benzene (1000 ml.) in portions and the extract is dried overnight with MgSO₄ and activated charcoal. The solution is filtered and the filtrate is adjusted to pH 3 with ether-HCl (cooled in ice bath). Petroleum ether (300 ml.) is added and the product oiled out of solution. The benzene-petroleum ether solution is decanted and the product is washed twice with anhydrous ether (scratching induced crystallization). The solid is recrystallized from ethanol (200 ml.) to yield: 32 g. (53%). A sample is recrystallized twice from isopropanol, m.p. 139°-143°.

Fifty milligrams of the above compound is administered to a human subject susceptible to secondarily generalized tonic clonic seizures to decrease the frequency and severity of these seizures.

EXAMPLE III

3-Diethylamino-2,2-diethylpropyl 5-(p-Nitrophenyl)-2-furoate Hydrochloride

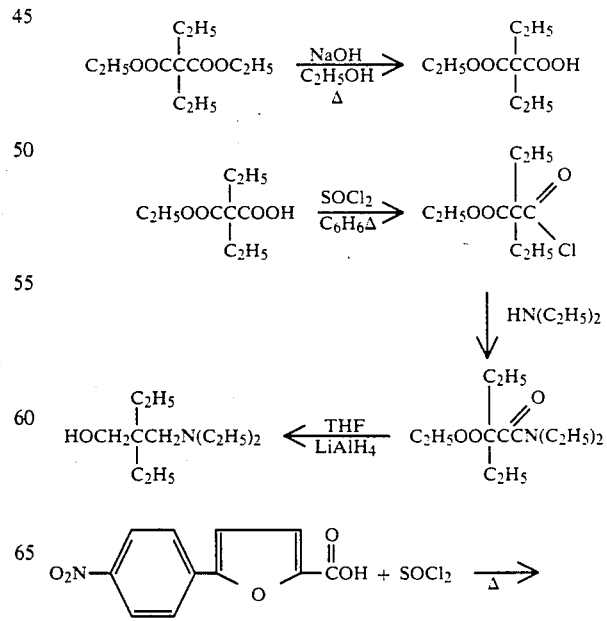

-continued

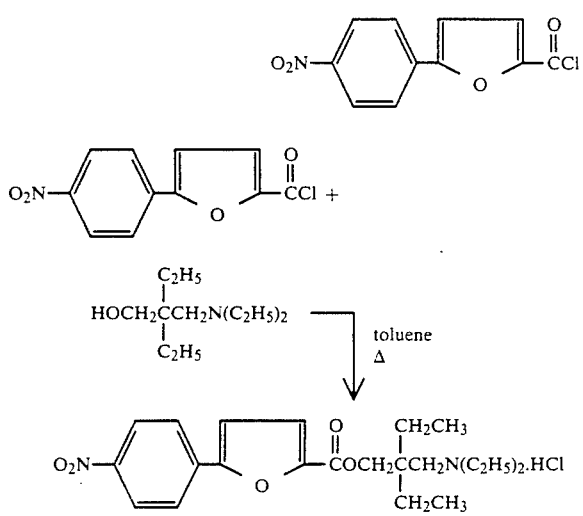

Monoethyl Diethylmalonate

A mixture of diethyl diethylmalonate (43 g., 0.20 mole) in absolute ethanol (300 ml.) and NaOH (10 g., 0.25 mole) is refluxed for 0.5 hour. The reaction mixture is stored at room temperature for 2 days, filtered to remove insoluble solid, and the filtrate is concentrated to dryness under reduced pressure at 70°–75° bath. The oily residue is dissolved in H$_2$O (50 ml.), acidified to a pH of 2–3 10% HCl with cooling, and is extracted with ether (240 ml.). The ether extract is dried over MgSO$_4$, is filtered, and is concentrated to dryness under reduced pressure at 50°–70° bath, to yield 37 g (98%) of monoethyl diethylmalonate.

Ethyl 2-(N,N-Diethylcarbamoyl)-2-ethylbutyrate

To a solution of monoethyl diethylmalonate (28 g. 0.15 mole) in dry benzene (300 ml.) is added SOCl$_2$ (15 ml., 0.21 mole) at 26°–28° C. in 2 min, with mechanical stirring. The reaction solution is gradually heated to 78° over 25 min, then is heated an additional 45 min at 85°–90°. The mixture is concentrated to dryness under reduced pressure, benzene (100 ml.) is added, and the mixture is again concentrated to dryness. The resultant oily residue dissolved in benzene (200 ml.) is treated dropwise with a solution of diethylamine (30 ml., 0.29 mole) in benzene (90 ml.) at 5°–15° over 17 min, and the reaction mixture is refluxed for 7 hours. The mixture is stored for 18 hours at room temperature and is filtered (to remove insoluble salt), is washed with benzene (50 ml.), is dried over MgSO$_4$ and activated charcoal for 15 min, is filtered, and is concentrated to dryness under reduced pressure (bath at 50°–60°). This will yield 29 g. (79%) of ethyl 2-(N,N-diethylcarbamoyl)-2-ethylbutyrate.

3-Diethylamino-2,2-diethylpropanol

To THF (300 ml.) is added LiAlH$_4$ (1.2 g), the mixture is refluxed for 20 min, and an additional quantity of LiAlH$_4$ (15.8 g., 0.42 mole) is added in two portions at 5°–21° over 1 min with mechanical stirring. The mixture is cooled to 5° and a solution of ethyl 2-(N,N-diethylcarbamoyl)-2-ethylbutyrate (29 g., 0.12 mole) in THF (80 ml.) is added at 5°–11° in 5 min. The temperature (exothermic) is allowed to rise to 60° over 12 min, is maintained at 49°–53° for 7 min, is heated gradually to reflux over 10 min, and then is refluxed for 6 hours. After it stands at room temperature for 18 hours, the reaction mixture is treated with Ac$_2$O (55 ml.) at 10°–20°, is stirred in an ice bath for 0.5 hour, is treated with H$_2$O (150 ml.) at 10°–18°, and finally is treated with CHCl$_3$ (250 ml.) at 10°–22° with slow stirring. The CHCl$_3$-layer is washed with H$_2$O (50 ml.), is dried over MgSO$_4$, is filtered, and is concentrated to dryness under reduced pressure. The resultant oil (30 ml.) is treated with 10% HCl (280 ml.) and is subjected to steam distillation for 1.3 hours, collecting 1 liter of distillate. The distillate is concentrated to 50 ml. by distillation under reduced pressure, is made basic with solid NaC$_2$O$_3$ to pH 8–9 in the cold, is extracted with ether, is dried over MgSO$_4$ and activated charcoal, is filtered, and is concentrated to dryness. The residual oil (12 g. plus 5.0 g. from previous run) is distilled at 60°–68°/1 mm to yield 11 g (35%) of 3-diethylamino-2,2-diethylpropanol.

3-Diethylamino-2,2-diethylpropyl 5-(p-nitrophenyl)-2-furoate Hydrochloride 5-(p-Nitrophenyl)-2-furoic acid (13.7 g., 0.059 mole) is added with rapid stirring to thionyl chloride (34 ml.), is heated until solution occurs, and is refluxed for 3 hrs. The mixture is stripped of excess thionyl chloride under reduced pressure. Benzene (100 ml.) is added, and the mixture is again stripped of solvent. The residue is treated with a solution of 3-diethylamino-2,2-diethylpropanol (11 g., 0.059 mole) in toluene (150 ml.), is refluxed for 3 hrs, cooled, is diluted with petroleum ether (150 ml.) and is stored for 18 hours at room temperature. The product is collected by filtration and is recrystallized from isopropanol, to yield 16 g (62%) of 3-diethylamino-2,2-diethylpropanol 5-(p-nitrophenyl)-2-furoate hydrochloride. A sample is recrystallized from isopropanol, m.p. 152°–156°.

One hundred milligrams of the above compound is administered to a human susceptible to partial complex seizures to decrease the frequency and severity of the seizures.

EXAMPLE IV

5-(p-Chlorophenyl)-2-furamide

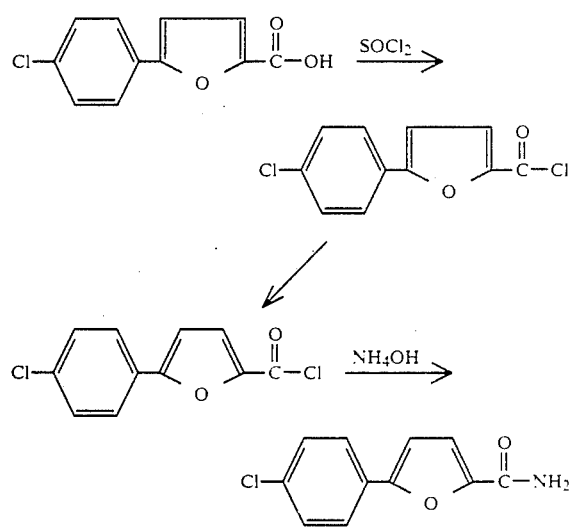

A mixture of 56 g. (0.25 mole) of 5-(p-chlorophenyl)-2-furoic acid and 100 ml. of SOCl$_2$ is refluxed for 3½ hours so that HCl gas evolves and there is dissolution.

The SOCl$_2$ is removed on a rotary evaporator. Benzene is added to the solid residue and is then removed on the rotary evaporator to give 5-(p-chlorophenyl)-2-furoyl chloride.

To 1000 ml. of cold, stirring NH$_4$OH, 63 g. (0.26 mole) of 5-(p-chlorophenyl)-2-furoyl chloride is added portionwise. The resulting mixture is stirred at ice bath temperature for 15 minutes and then is stored at room temperature for 18 hours. The solid is filtered, is washed with water and is dried at 60° to yield 56 g. (97%).

Fifty milligrams of the above compound is administered to a human susceptible to partial seizures with elementary symptomatology to decrease the frequency and severity of the seizures.

EXAMPLE V

1-[5-(4-Nitrophenyl)-2-furanylcarbonyl]piperazine Hydrobromide washed in hexane and is air dried to yield 104 g. (73%) of preparation of phenylmethyl 1-piperazinecarboxylate hydrochloride.

B. 4-[5-(4-Nitrophenyl)-2-furanylcarbonyl]-1-(phenylmethoxycarbonyl) piperazine

An 8 g (0.03 mole) sample of phenylmethyl 1-piperazinecarboxylate hydrochloride is dissolved in a minimal amount of H$_2$O and is made strongly basic with 3N NaOH solution. This resulting mixture is extracted with ether. The ether is dried over MgSO$_4$ and the solvent is then removed on a rotary evaporator to yield the free base as a residual oil. This oil, 3.5 g. (0.035 mole) of triethylamine, and 75 ml. of toluene is heated to 80°. At a temperature of 75°–80° a warm solution of 8 g. (0.03 mole) of 5-(4-nitrophenyl)-2-furoyl chloride in 150 ml. of toluene is added dropwise. The resulting mixture is heated for 3 hr. at steam bath temperature and then is allowed to cool to room temperature. A small amount

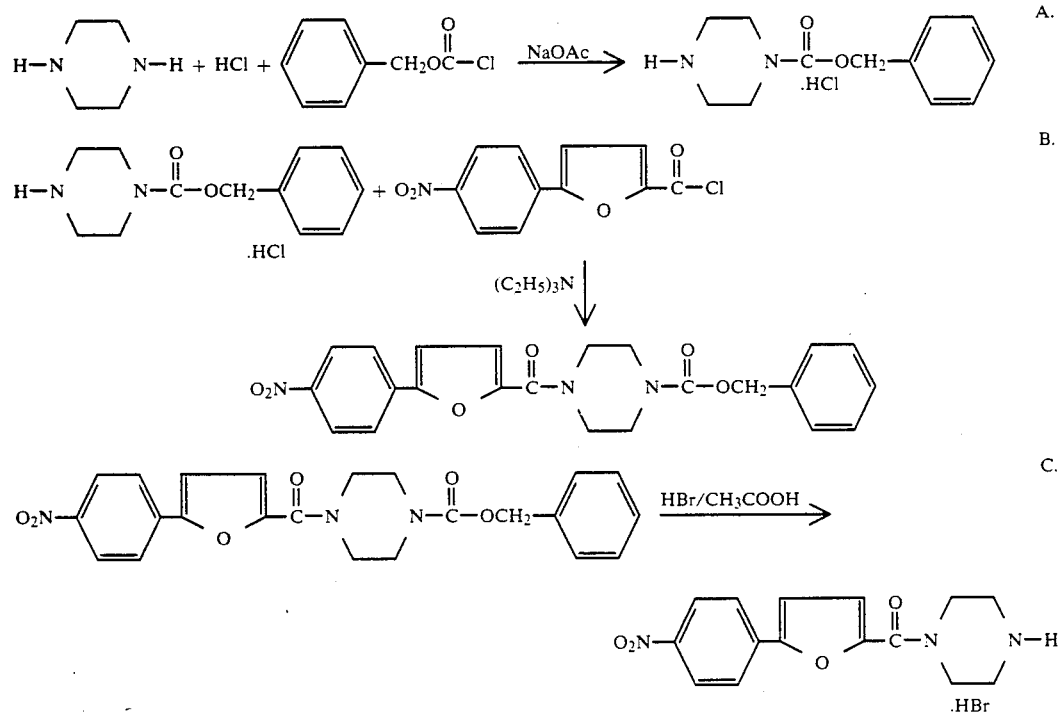

A. Preparation of Phenylmethyl 1-piperazinecarboxylate Hydrochloride

A solution of 47 g. (0.55 mole) of anhydrous piperazine in 550 ml. of H$_2$O is adjusted to a pH of 2 by the portionwise addition of 95 ml. of concentrated hydrochloric acid. Acetone (550 ml.) is added. A few drops from a solution of 118 g. of anhydrous NaOAc in 300 ml. of H$_2$O is added to adjust the pH to 3. Carbenzoxy chloride (100 g., 0.590 mole) is added simultaneously to the remaining sodium acetate solution. The sodium acetate solution is added by means of a pH stat with the pH of the reactions being kept between 3 to 3.2. The reaction is stirred at ambient temperature for 4 hr. The reaction mixture is set for vacuum distillation with the volume of the reaction being reduced by two-thirds. The resulting solid (1,4-bis[(phenylmethoxy)carbonyl]) is filtered and is set aside. The filtrate is taken to dryness on a rotary evaporator to yield a white solid. This solid is extracted with 3×500 ml. portions of refluxing ethanol. The combined extracts are concentrated on a rotary evaporator to yield a residual solid. This solid is of solid is filtered and discarded. The filtrate is taken to dryness on a rotary evaporator to yield a residual oil. This oil is triturated in ethyl acetate with a solid forming. The solid is filtered and is air dried to yield 10.5 g. (80%) of 4-[5-(4-Nitrophenyl)-2-furanylcarbonyl]-1(phenylmethoxycarbonyl) piperazine.

C. 1-[5-(4-Nitrophenyl)-2-furanylcarbonyl]piperazine Hydrobromide

To a 20 g. (0.46 mole) sample of the above compound is added 400 ml. of a saturated solution of HBr/CH$_3$COOH. The resulting solution is slowly warmed to 40° with a precipitate forming. Stir this mixture at 40°–45° for 30 min, stir at ambient temperature for 30 min and then cool in an ice bath. The solid is filtered and then is stirred in refluxing methanol. The mixture is cooled and then is filtered. The solid is dried in a desiccator over NaOH to yield 17 g. (97%).

One hundred milligrams of the above compound is administered to a human susceptible to generalized

EXAMPLE VI

N-[3-(4-Morpholinyl)propanyl]-5-(4-bromophenyl)-2-furancarboxamide

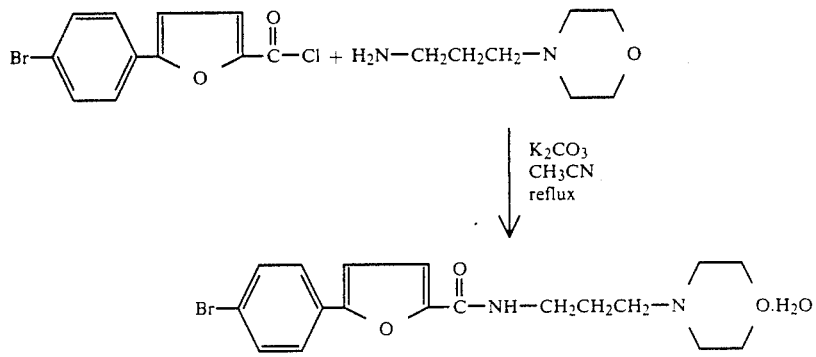

A mixture of 4.06 g of 5-(4-bromphenyl)-2-furancarboxylic acid chloride and 2.55 g of N-(3-aminopropyl)-morpholine is refluxed 6 hr with 3.0 g of anhydrous potassium carbonate in 50 ml of acetonitrile. The mixture is allowed to stir at room temperature overnight. Solvents are then evaporated and the residue is triturated with ethyl ether followed by evaporation again. This process is repeated several times. A solution of the residue in ethyl ether is allowed to stand overnight whereupon crystals are formed. After three recrystallizations from ethyl acetate, the product, 2.47 g (37.5%), melts at 8°–100° C. The CI and EI mass spec. are consistent with the proposed structure. The latter showed $M^+ = 393$.

Fifty milligrams of the above compound is administered to a human subject susceptible to simple partial seizures to decrease the frequency and severity of these seizures.

EXAMPLE VII

N-[3-(4-Morpholinyl)propyl]-5-(2,4-dichlorophenyl)-2-furancarboxamide Hydrochloride Hydrate

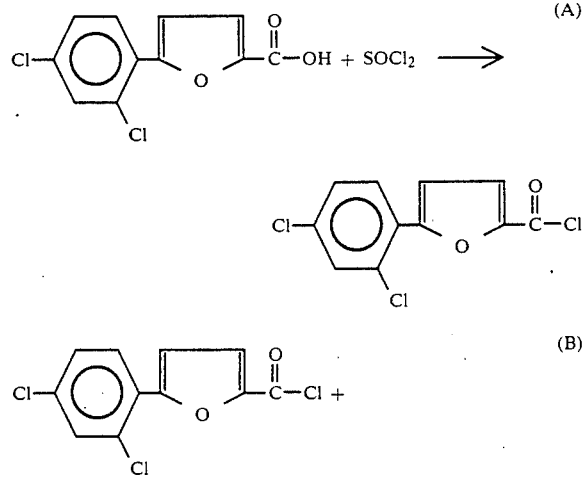

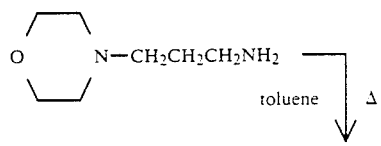

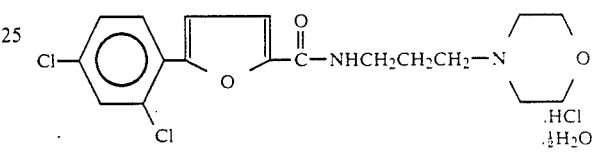

A) Preparation of 5-(2,4-Dichlorophenyl)-2-furanoyl Chloride

A solution of 28.28 g (0.11 moles) of 5-(2,4-dichlorophenyl)-2-furancarboxylic acid in 43 ml of thionyl chloride is heated at reflux for 3 hours. The solvent is removed and the residue is treated with 100 ml of toluene. The solvent is removed and the residue is carried on directly to the next step of the reaction.

B) Preparation of N-[3-(4-Morpholinyl)propyl]-5-(2,4-dichlorophenyl)-2-furancarboxamide Hydrochloride Hydrate A solution of 15.86 g (0.11 mole) of N-(3-aminopropyl)morpholine and the above prepared residue in 600 ml of toluene is heated at reflux for 3 hours and is then allowed to stand at room temperature overnight. Petroleum ether (400 ml) is added to the reaction mixture and is then allowed to stand at room temperature overnight. A solid is filtered and dissolved in 600 ml of isopropanol followed by adding 1-liter of ethyl ether. Upon cooling a solid forms which is filtered and recrystallized from absolute ethanol. Five additional recrystallizations are required to obtain the desired product which weighs 6.370 g (13.5%); m.p. 201°–204° C.

One hundred milligrams of the above compound is administered to a human susceptible to partial complex seizures to decrease the frequency and severity of the seizures.

EXAMPLE VIII

A human subject with a history of complex partial seizures is given 25 mg of 3-diethylamino-2,2-dimethylpropyl 5-(3trifluoromethylphenyl)-2-furoate hydrochloride (from U.S. Pat. No. 3,856,825) three times per day. The administration of 3-diethylamino-2,2-dimethylpropyl 5-(3-trifluoromethylphenyl)-2-furoate hydrochloride decreases the frequency and severity of these seizures. This therapy extends for the lifetime of the human subject. In the above example, 3-diethylamino-2,2-dimethylpropyl 5-(p-nitrophenyl)-2-furoate hydrochloride; 3-diethylamino-2,2-dimethylpropyl 5-(3,4-dichlorophenyl)-2-furoate hydrochloride; 3-diethylamino-2,2-dimethylpropyl 5-(4-chloro-2-nitrophenyl)-2-furoate hydrochloride; 3-diethylamino-2,2-dimethylpropyl 5-(m-trifluoromethylphenyl)-2-furoate hydrochloride; 3-diethylamino-2,2-dimethylpropyl 5-(m-nitrophenyl)-2-furoate hydrochloride; 3-diethylamino-2,2-dimethylpropyl 5-(p-bromophenyl)-2-furoate hydrochloride; 3-diethylamino-2,2-dimethylpropyl 5-(p-methoxyphenyl)-2-furoate hydrochloride; 3-diethylamino-2,2-dimethylpropyl 5-(m-methoxyphenyl)-2-furoate fumarate; 3-diethylamino-2,2-dimethylpropyl 5-(p-methylphenyl)-2-furoate fumarate (P-768); 3-diethylamino-2,2-dimethylpropyl 5-(3,4-difluorophenyl)-2-furancarboxylate hydrochloride hemihydrate; 1 methyl-4-piperidyl 5-(p-chlorophenyl)-2-furoate hydrochloride; 5-(p-chlorophenyl)-N,N-dimethyl-2-furamide; 5-(p-chlorophenyl)-2-furoic acid 1-isopropylhydrazide; 5-(4-aminophenyl)-N-[2-(diethylamino)ethyl]-2-furancarboxamine hydrochloride; 5-(4-bromophenyl)-N-[3-(4-morpholinyl)propyl]-2-furancarboxamide hydrate; N-[3-(diethylamino)-2,2-dimethylpropyl]-5-(4-trifluoromethyl-phenyl)-2-furancarboxamide (Z)-2-butenedioic acid salt; 5-(2,4-dichlorophenyl)-N-[3-(4-morpholinyl)propyl]-2-furancarboxamide hydrochloride hydrate; are substituted for 3-diethylamino-2,2-dimethylpropyl 5-(3-trifluoromethylphenyl)-2-furoate hydrochloride with substantially similar results.

EXAMPLE IX

A human subject suffering from generalized tonic-clonic seizures is given 50 mg of 3-diethylamino-2,2-dimethylpropyl 5-(p-methylphenyl)-2-furoate fumarate twice a day. Administration of the above compound inhibits these seizures completely. The human subject undergoes chronic therapy with this agent.

EXAMPLE X

A human subject who is admitted to a hospital emergency room with a seizure of unknown origin manifested by uncontrolled arm and leg movements, is administered 50 mg of 3-diethylamino-2,2-dimethylpropyl 5-(p-fluorophenyl)-2-furoate hydrochloride intravenously in a suitable solution for intravenous injection. This causes the seizure to subside within a few minutes of injection. This therapy is administered only as an emergency measure to a human subject presently experiencing a seizure whose origin is not known.

What is claimed is:

1. A method of preventing epileptic seizures in a human or mammal subject susceptible to said seizures, comprising systemically administering to said subject a safe and effective amount of a compound of the formula:

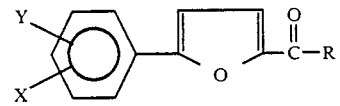

wherein
(a) X is halo or hydrogen, and Y is a substituent selected from the group consisting of unsubstituted or halogen-substituted methyl, halo, nitro, amino, and methoxy; and
(b) R is $N(R^3)_2$, $OR^1N(R^3)_2$, $N(R^2)R^1N(R^3)_2$, or $N(R^2)N(R^3)_2$; where
$R^1$ is $C_1$–$C_3$ alkylene which is unsubstituted or substituted with $C_1$–$C_2$ alkyl;
$R^2$ is hydrogen or lower alkyl; and
each $R^3$ is, independently, hydrogen or lower alkyl;
or a pharmaceutically-acceptable salt thereof.

2. A method of preventing epileptic seizures in a human or mammal subject susceptible to said seizures, according to claim 1 wherein X is hydrogen.

3. A method of preventing epileptic seizures in a human or mammal subject susceptible to said seizures, according to claim 1 wherein X is halo.

4. A method of preventing epileptic seizures in a human or mammal subject susceptible to said seizures, according to claim 1 wherein Y is halosubstituted methyl.

5. A method of preventing epileptic seizures in a human or mammal subject susceptible to said seizures, according to claim 1 wherein Y is trifluoromethyl.

6. A method of preventing epileptic seizures in a human or mammal subject susceptible to said seizures, according to claim 1 wherein R is $N(R^3)_2$, $N(R^2)R^1N(R^3)_2$ or $N(R^2)N(R^3)_2$.

7. A method of preventing epileptic seizures in a human or mammal subject susceptible to said seizures, according to claim 1 wherein R is $OR^1N(R^3)_2$.

8. A method of preventing epileptic seizures in a human or mammal subject susceptible to said seizures, according to claim 2, wherein R is 3-diethylamino-2,2-dimethylpropoxy and Y is selected from the group consisting of: para- and meta-fluoro, para- and meta-chloro, para- and meta-trifluoromethyl, meta-nitro, para- and meta-bromo, para- and meta-methoxy, para methyl, para-amino and ortho-chloro.

9. A method of preventing epileptic seizures in a human or mammal subject susceptible to said seizures according to claim 3 wherein R is 3-diethylamino-2,2-dimethylpropoxy and X and Y are the same substituent selected from the group consisting of chloro and fluoro.

10. A method of preventing epileptic seizures in a human or mammal susceptible to said seizures according to claim 8 wherein Y is selected from the group consisting of: para- and meta-fluoro, para- and meta-chloro, para- and meta-triflouromethyl, meta-nitro, para- and meta-bromo, para- and meta-methoxy, and para-methyl.

11. A method of preventing epileptic seizures in a human or mammal subject susceptible to said seizures, comprising systemically administering to said subject a safe and effective amount of 3-diethylamino-2,2-dimethylpropyl 5-(p-trifluoromethylphenyl)-2-furoate hydrochloride.

* * * * *